United States Patent [19]

Van Rheenen et al.

[11] 4,451,404
[45] May 29, 1984

[54] 16β-METHYL STEROID PROCESS

[75] Inventors: Verlan H. Van Rheenen, Portage; Joseph M. Timko, Kalamazoo, both of Mich.

[73] Assignee: The Upjohn Company, Kalamazoo, Mich.

[21] Appl. No.: 465,141

[22] Filed: Feb. 9, 1983

[51] Int. Cl.³ .............................. C07J 1/00; C07J 9/00
[52] U.S. Cl. .............................. 260/397.45; 260/397.1
[58] Field of Search ......................... 260/397.45, 397.1

[56] References Cited

U.S. PATENT DOCUMENTS 3,039,528  6/1962  Arth et al. ......................... 260/397.4
3,704,253  11/1972  Stein et al. ........................ 260/397.4
4,216,159  8/1980  Hessler et al. .................... 260/397.1

OTHER PUBLICATIONS

P. de Ruggieri et al., *Gazz Chim. Ital.*, vol. 91, p. 672, (1961).

G. Neef et al., *J. Org. Chem.*, vol. 43, p. 4679, (1978).

*Primary Examiner*—Elbert L. Roberts
*Attorney, Agent, or Firm*—Bruce Stein

[57] ABSTRACT $\Delta^4$-3-keto, $\Delta^{1,4}$-3-keto and 3β-hydroxy 17-keto steroids (I) are transformed into the corresponding 16-β-methyl-17-keto steroids (IV) by first activating the C-16 position, then methylating. By protecting the C-3 position of the $\Delta^4$-3-keto and 3β-hydroxy steroids the yields are greatly increased.

26 Claims, No Drawings

16β-METHYL STEROID PROCESS

DESCRIPTION

Background of the Invention

The transformation of 17-keto steroids (I) to the corresponding 16β-methyl-17-keto steroid (IV) is well known to those skilled in the art. See, for example, U.S. Pat. Nos. 3,039,528, 3,704,253 and Gazz. Chim. Ital. 91, 672 (1961). Most of the processes produce some 16α-methyl isomer. G. Neef in J. Org. Chem. 43, 4679 (1978) determined that the thermodynamic equilibrium mixture of 16β-methyl/16α-methyl was 78.5/21.5 for 3β-acetoxy-16-methylandrost-5-en-17-one.

P. deRuggiere et al, Gazz. Chim. Ital. 91, 672 (1961) on p. 678 discloses a three-step process for the transformation of a 17-keto steroid (I) to the corresponding 16β-methyl-17-keto steroid (IV). The process involves glyoxalation, methylation and deglyoxalation. While deRuggieri does not disclose the 16β-methyl/16α-methyl product ratio, he obtained a low yield (45.8%). Because of the importance of 16β-methyl-17-keto steroids (IV) as starting material for production of 16β-methyl corticoids, those skilled in the art continued to try and add a 16-methyl group to a 17-keto steroid stereoselectively in the β-configuration and obtain high yields.

The improved process of the present invention greatly increases the yield of the 16β-methyl product by protecting the $\Delta^4$-3-keto and 3β-hydroxy-$\Delta^5$-steroid starting materials at the $C_3$ position whereby the process of the present invention produces a 16β-methyl/16α-methyl ratio of greater than 90/10 and up to about 95/5.

SUMMARY OF THE INVENTION

Disclosed is a process for the preparation of 16β-methyl-17-keto steroids selected from the group consisting of compounds of the formula (IVAa, IVAb, IVCa) which comprises (1) contacting a 17-keto steroid selected from the group consisting of compounds of the formula (IAa, IAb, ICa) with a $C_{16}$ activating agent in the presence of an alkali metal alkoxide to produce an anion of a 16-substituted steroid of the formula (IIAa, IIAb, IICa)

(2) contacting the anion of the 16-substituted steroid (II) from step (1) with a methylating agent to produce a 16-methyl-16-substituted steroid of the formula (IIIAa, IIIAb, IIICa) and (3) contacting the 16-methyl-16-substituted steroid from step (2) with a strong base in an alcohol containing solvent.

Also disclosed is a process for the preparation of a 16β-methyl-17-keto steroid of the formula (IVB) which comprises (1) contacting a 17-keto steroid of the formula (IB) with a $C_{16}$ activating agent in the prsence of an alkali metal alkoxide to produce an anion of a 16-substituted steroid of the formula (IIB)

(2) contacting the anion of the 16-substituted steroid (IIB) with a methylating agent to produce a 16-methyl-16-substituted steroid of the formula (IIIB) and (3) contacting the 16-methyl-16-substituted steroid with a strong base in an alcohol containing solvent.

DETAILED DESCRIPTION OF THE INVENTION

The 17-keto steroid (IA-IC) starting materials are well known to those skilled in the art or can be readily prepared from known compounds by methods well known to those skilled in the art.

In Gazz. Chim. Ital. deRuggiere et al reacted a 3β-hydroxy-17-keto steroid and produced a 16β-methyl-17-keto steroid but only in 45.8% yield. The present invention significantly improves the yield of the 16β-methyl-17-keto steroid (IV) by protecting the $C_3$ functionality of the starting material. The $\Delta^4$-3-keto (A) and 3β-hydroxy (C) 17-keto steroid (I) starting materials must have the $C_3$ functionality protected to obtain high yields with a good 16β/16α-methyl isomer ratio. The $\Delta^{1,4}$-3-keto 17-keto steroid (IB) starting material does not need the $C_3$ ketone protected. The $\Delta^4$-3-keto-17-keto steroids (IA) are protected as the enol ether (Aa) or ketal (Ab). The 3β-hydroxy-$\Delta^5$ steroids (IC) are protected as the ether (Ca). The preferred enol ether (Aa) is the methyl or ethyl ether. The preferred ketal (Ab) is the ethylene ketal. The preferred protecting group for the 3β-hydroxy-$\Delta^5$ steroids (C) is the methyl, or THP ether. The enol ethers are prepared by methods well known to those skilled in the art, see J. Org. Chem. 26, 3925 (1961), Steroid Reactions, Edited by Carl Djerassi, Holden-Day, San Francisco 1963, pp. 42–45 and U.S. Pat. No. 3,516,991 (Preparation 1). The ketals (b) are also prepared by well known methods, see Steroid Reactions, supra, pp. 11–14.

In order to methylate the 17-keto steroid (I) at $C_{16}$ the appropriate form of the 17-keto steroid (I) is first activated by forming a 16-substituted steroid (II). The 17-keto steroid (I) is reacted with a $C_{16}$ activating agent selected from the group consisting of dialkyloxalates, alkyl formates or dialkylcarbonates where the alkyl portion is one through 3 carbon atoms with an alkali metal alkoxide in an inert organic solvent at a temperature from about $-20°$ to the reflux temperature of the inert organic solvent. It is preferred that the $C_{16}$ activating agent be dialkyloxalate, more preferably dimethyl or diethyl oxalate. The alkali metal alkoxides include lithium, sodium and potassium with sodium being preferred. The alkyl portion of the alkoxide includes alkyl of 1 through 4 carbon atoms. The preferred alkali metal alkoxides are sodium methoxide and sodium ethoxide. Inert organic solvents include methylene chloride, THF, diethyl ether and dimethoxyethane. The preferred temperature range is from about 0° to about 25°. The 16-substituted steroid (II) can be isolated and purified. In performing the next step, methylation, it is not necessary to purify the 16-substituted steroid (II) and it is preferable to perform the next step without isolation and purification of its 16-substituted steroid (II). The 16-substituted steroid (II) is actually present as the alkali metal salt of an anion of the $C_3$ protected form (II). If it is desired to isolate the 16-substituted steroid (II), one would acidify so as to transform the anion to the non-charged 16-substituted steroid (II). Before performing the next step, methylation, the 16-substituted steroid (II) would again have to be subjected to alkaline conditions.

The 16-substituted steroid is then methylated to produce a 16-methyl-16-substituted steroid (III). Methylation is performed by reacting the alkali metal salt of its $C_3$ protected steroid (II) with a methyl halide in an inert organic solvent from about $-20°$ to the reflux temperature of its inert organic solvent or the reaction vessel may be sealed and run at temperatures up to about 150°. Methyl halides include methyl iodide and methyl bromide with methyl iodide preferred. Inert organic solvents include acetone, THF, diethyl ether, methylethylketone and dimethyoxyethane; acetone is the preferred organic solvent. Methylene chloride retards the methylation reaction. Neutralization of the excess sodium methylate with an acid such as acetic acid and addition of potassium carbonate reduces by-product formation during methylation. It is preferred to use an excess of methylating agent. With methyl iodide preferred reaction conditions are 1.1–5.0 equivalents at 50°–75° in acetone in a sealed reaction vessel. A full 5.0 equivalents of methyl iodide are used to promote methylation at 55° in 20–24 hours. If reaction conditions are chosen such that methylation takes 48 hours, the reaction shows considerable hydrolysis of the 3-enol ester of the $\Delta^4$-3-keto (A) steroids. When methyl iodide is used as the methylating agent, methyl bromide can be added to the reaction mixture when the reaction is complete. The excess methyl iodide and organic solvent are removed under reduced pressure to give the 16-methyl-16-substituted steroid (III) which can be purified if desired. However, it is not necessary or even desirable to purify its 16-methyl-16-substituted steroid (III) but rather it is preferable to perform the third and last step directly on the impure 16-methyl-16-substituted steroid (III).

The 16-methyl-16-substituted (III) is transformed to the desired 16$\beta$-methyl-17-keto steroid (IV) by reaction with a strong base in an alcoholic solvent (ROH where R is alkyl of 1 through 5 carbon atoms). Strong bases include, for example, alkali metal (lithium, sodium, potassium) alkoxides (where the alkyl portion of the alkoxide includes alkyl of 1 through 4 carbon atoms), alkali metal (lithium, sodium, potassium) hydroxides and alkali metal (lithium, sodium, potassium) carbonates. It is preferable to use no more than 1 equivalent of base, with 1.0 equivalents being preferred. The preferred system is sodium methoxide in methanol. Water can be present in the system. Alternatively, an inert solvent such as THF, diethyl ether, methylene chloride or dimethoxyethane, or mixtures thereof containing one of the above-mentioned bases and an alcohol co-solvent may be used.

It is realized that in this third step, the deglyoxalation reaction, both 16$\beta$-methyl and 16$\alpha$-methyl isomers are produced. The reaction temperature is critical to obtaining an isomer ratio of greater than or equal to 90% of the 16$\beta$-methyl (desired) to the 16$\alpha$-methyl (undesired) methylated-17-keto steroid (IV). At very low temperatures unwanted side reactions can occur and at high temperatures epimerization of the 16$\beta$-methyl group occurs. Temperatures between about $-20°$ and about 25° are preferable, with about $-5°$ to about 10° being more preferred. The optimum temperature for each reaction will depend on the particular 16-methyl-16-substituted steroid (III), the particular strong base and the particular solvent as is well known to those skilled in the art and therefore may vary slightly from the $-5°$ to 10° generally preferred range.

With the $\Delta^4$-3-keto steroid (A) and the 3$\beta$-hydroxy-$\Delta^5$ steroids (C) its 16$\beta$-methyl-17-keto product is in the $C_3$ protected form. These $C_3$ protected steroids can either be used in their $C_3$ protected forms as discussed below or can be readily transformed to the free or unprotected form by means well known to those skilled in the art.

The 16$\beta$-methyl-17-keto steroids (IVA-C) are useful intermediates in the production of the commercially valuable 16$\beta$-methyl anti-inflammatory corticoids such as betamethasone, meprednisone, beclomethasone and diflorasone diacetate, see U.S. Pat. Nos. 4,041,055, 4,216,159, 4,284,827 and 4,342,702. The 3$\beta$-hydroxy-16$\beta$-methyl-17-keto steroids (IVC) can be readily oxidized to the corresponding $\Delta^4$-3-keto-16$\beta$-methyl-17-keto steroid (IVA) which in turn can be dehydrogenated by means well known to those skilled in the art to the corresponding $\Delta^{1,4}$-3-keto-16$\beta$-methyl-17-keto steroid (IVB).

DEFINITIONS

The definitions and explanations below are for the terms as used throughout the entire patent application including both the specification and the claims.

All temperatures are in degrees Centigrade.

TLC refers to thin-layer chromatography.

THF refers to tetrahydrofuran.

THP refers to tetrahydropyran.

p-TSA refers to p-toluenesulfonic acid monohydrate.

NMR refers to nuclear (proton) magnetic resonance spectroscopy, chemical shifts are reported in ppm ($\delta$) downfield from TMS.

TMS refers to tetramethylsilane.

When solvent pairs are used, the ratio of solvents used is volume/volume (v/v).

When the term "alkyl of _ through _ carbon atoms" is used, it means and includes isomers thereof where such exist.

R is a hydrogen atom or —CO—OR' or —OR'.

R' is alkyl of 1 through 5 carbon atoms.

$R_3$ is alkyl of 1 through 5 carbon atoms.

$R_6$ is a hydrogen or fluorine atom.

$R_{11}$ is a hydrogen atom, nothing ($\Delta^{9(11)}$), or a hydroxyl group ($\alpha$ or $\beta$).

⎓⎓⎓ is a single or double bond.

EXAMPLES

Without further elaboration, it is believed that one skilled in the art can, using the preceding description, practice the present invention to its fullest extent. The following detailed examples describe how to prepare the various compounds and/or perform the various processes of the invention and are to be construed as merely illustrative, and not limitations of the preceding disclosure in any way whatsoever. Those skilled in the art will promptly recognize appropriate variations from the procedures both as to reactants and as to reaction conditions and techniques.

EXAMPLE 1

3-Methoxy-16-(methyloxalyl)androsta-3,5,9(11)-trien-17-one sodium salt (IIAa)

3-Methoxyandrost-3,5,9(11)-trien-17-one (IAa), U.S. Pat. No. 3,516,991 (29.84 gms) methylene chloride (200 ml) and diethyloxalate (16.1 gms) are cooled to 0°. Solid sodium methoxide (6.5 gms) is added. The cooling bath is removed and the mixture stirred at 20°–25°. After one hour, TLC indicates some starting material remains. Additional sodium methoxide (1.08 gms) is added. After an additional hour, TLC shows no starting material remained. Sodium bicarbonate (3.6 gms) is added, the solution stirred for 10 minutes and the solvent removed at a reduced pressure to give the title compound.

EXAMPLE 2

3-Methoxy-16-methyl-16-(methyloxalyl)androst-3,5,9(11)-trien-17-one (IIIAa)

Acetone (200 ml) is added to 3-methoxy-16-(methyloxalyl)androst-3,5,9(11)-trien-17-one sodium salt (IIIAa, Example 1) to produce a thin slurry. Methyl iodide (70.95 gms) is added and the flask stoppered with a rubber septum sealed with parafilm and heated to 65°. After 18 hours, the mixture is cooled to 20°–25°. TLC shows no remaining glyoxalate starting material. In order to regenerate the methyl iodide, methyl bromide in acetone (1 equivalent, 1.0 M, 100 ml) is added and the mixture stirred 15 minutes. The organic solvent and methyl iodide are removed under reduced pressure to give the title compound as a solid.

EXAMPLE 3

3-Methoxy-16β-methylandrost-3,5,9(11)-trien-17-one (IVAa)

To the crude methylated glyoxalate as a solid was added methanol (300 ml) and the resulting slurry cooled to −10° utilizing overhead stirring. A methanolic solution of sodium methoxide is then added (25%, 23 ml). After 15 minutes at −10°, reaction is complete as measured by TLC. The slurry is poured into water (300 ml) at 5° containing acetic acid (6.9 ml); the mixture is filtered and the solid washed with water (100 ml) and dried under reduced pressure at 50° to give the title compound, m.p. 124°–129°; NMR (CDCl$_3$) 0.83, 1.13, 1.18, 3.53, 5.13, 5.27 and 5.48 δ

EXAMPLE 4

3-Methoxy-16-(methyloxalyl)androsta-3,5-dien-17-one-sodium salt (IIAa)

Methylene chloride (133 ml), diethyloxalate (10.7 gms) and 3-methoxyandrost-3,5-dien-17-one (IAa, 20 gms) are mixed and cooled to 0°. Solid sodium methoxide (4.3 gms) is added, the cooling bath removed and the reaction stirred at 20°–25° overnight. Sodium methoxide (0.71 gms) is added and the mixture stirred 2.75 hours. Additional sodium methoxide (0.71 gms) is added and the mixture stirred an additional 2 hours. After two hours of stirring, sodium methoxide (0.35 gms) is added followed by diethyloxalate (1.076 gms), the mixture stirred an additional 30 minutes following which sodium carbonate (1.7 gms) is added; the mixture stirred an additional 30 minutes after which the methylene chloride is removed under reduced pressure to give the title compound.

EXAMPLE 5

3-Methoxy-16-methyl-16-(methyloxalyl)androst-3,5-dien-17-one (IIIAa)

Acetone (133 ml) is added to 3-methoxy-16-(methyloxalyl)androst-3,5-dien-17-one sodium salt (II, Example 4) followed by methyl iodide (20.5 ml), the flask stoppered by rubber septum and sealed with parafilm and heated to 55° for 17 hours. The reaction is complete as measured by TLC. The mixture is cooled to 20°–25° and methyl bromide in acetone (1.0 equivalent) is added, the reaction mixture stirred 10 minutes and then concentrated under reduced pressure to give the title compound.

EXAMPLE 6

3-Methoxy-16β-methylandrost-3,5-diene-17-one (IVAa)

Methanol (133 ml) is added to 3-methoxy-16-methyl-16-(methyloxalyl)androst-3,5-diene-17-one (III, Example 5). The slurry is cooled to 0° with an ice bath and one equivalent of methanolic sodium methoxide (25%, sodium methoxide/methanol, 15.1 ml) is added. After one hour, the reaction is complete as measured by TLC. The mixture is poured into ice water (135 ml) containing acetic acid (4.9 ml). The solid material is obtained by filtration and dried under reduced pressure at 50° overnight to give the title compound. m.p. 149°–167°; NMR (CDCl$_3$) 0.87, 1.00, 1.22, 3.56, 5.12 and 5.23 δ.

EXAMPLE 7

3-Hydroxyandrost-5-ene-17-one THP ether (ICa)

3-Hydroxyandrost-5-ene-17-one (dehydroepiandrosterone, 20 gms) is dissolved in methylene chloride (140 ml) and cooled to 0°. Dihydropyran (6.4 gms, 1.1 equivalent) is added followed by pyridinium tosylate (0.17 gms). The reaction is warmed to about 20°–25° and stirred for two hours following which it is cooled and pyridinium tosylate (6.4 gms) and dihydropyran (0.58 gms) are added. The mixture is stirred for one hour at 20°–25°, then recooled, following which a few crystals of p-TSA are added. The reaction is then stirred at 20°–25° for 48 hours then quenched with half saturated aqueous sodium chloride, the organic layer separated, dried over sodium sulfate and concentrated under reduced pressure to give the title compound, NMR(CDCl$_3$) 0.88, 1.03, 1.72 and 5.33 δ.

EXAMPLE 8

3-Hydroxy-16-(methyloxalyl)androst-5-ene-17-one THP ether (IICa)

Methylene chloride (95 ml), 3-hydroxyandrost-5-ene-17-one THP ether (ICa, Example 7, 17.58 gms) and diethyloxalate (7.6 gms) are mixed and cooled to 0°. Solid sodium methoxide (3 gms) is added and stirred at 20°–25° for 2.5 hours. Additional sodium methoxide (0.51 gms) is added and the reaction stirred overnight. Additional sodium methoxide (0.5 gms) is added. The excess sodium methoxide is neutralized with sodium carbonate (1.2 gms). After stirring for 30 minutes the methylene chloride is removed under reduced pressure to give the title compound.

EXAMPLE 9

3-Hydroxy-16-methyl-16-(methyloxalyl)androst-5-ene-17-one THP ether (IIICa)

Acetone (95 ml) is added to 3-hydroxy-16-(methyloxalyl)androst-5-ene-17-one THP ether sodium salt (IICa, Example 8) followed by five equivalents of methyl iodide (14.7 ml). The flask is stoppered with a rubber septum, sealed with parafilm and heated to 55° for nineteen hours. Methyl bromide is bubbled into the reaction mixture. The reaction mixture is then concentrated under reduced pressure to give the title compound.

EXAMPLE 10

3β-Hydroxy-16β-methylandrost-5-ene-17-one THP ether (IVCa)

3β-Hydroxy-16-methyl-16-(methyloxalyl)androst-5-ene-17-one THP ether (IIIC, Example 9) is slurried in methanol (100 ml) at 0°. One equivalent of sodium methoxide (25% sodium methoxide/methanol, 10 ml) is added. After 30 minutes, the slurry is poured into ice water (100 ml) containing acetic acid (2.0 ml) and the mixture filtered. The solid is washed with ice water (30 ml) and dried under reduced pressure at 50° overnight to give a solid which is purified by column chromatography over silica gel eluting with 2.5% acetone in methylene chloride. The appropriate fractions are pooled and concentrated to give the title compound, NMR, (CDCl$_3$), 0.82, 1.02, 1.19, 4.73, 5.38 δ.
CHART A
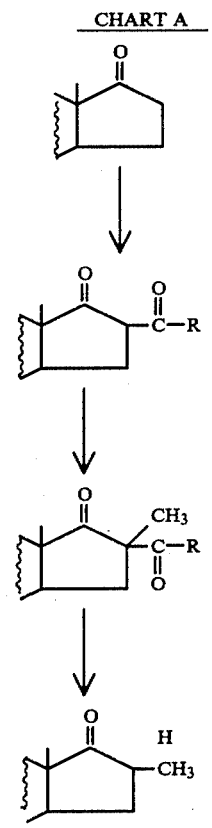
CHART B
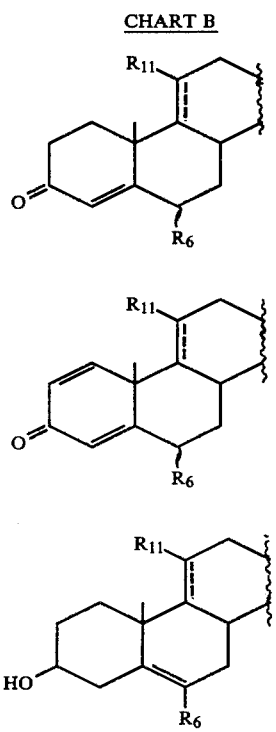
CHART C
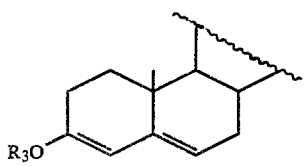
(Aa)
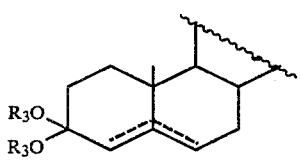
(Ab)
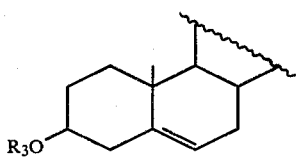
(Ca)
We claim:
1. A process for the preparation of 16β-methyl-17-keto steroids selected from the group consisting of
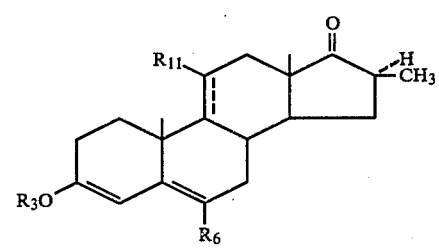
(IVAa)
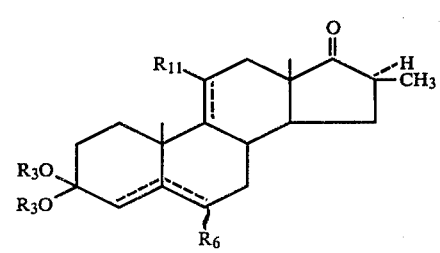
(IVAb)
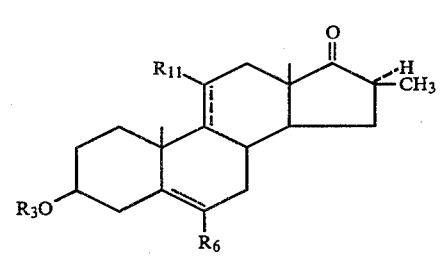
(IVCa)
which comprises
(1) contacting a 17-keto steroid selected from the group consisting of

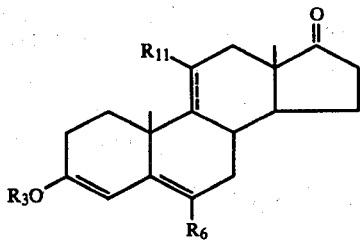
(IAa)

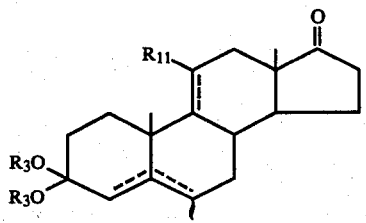
(IAb)

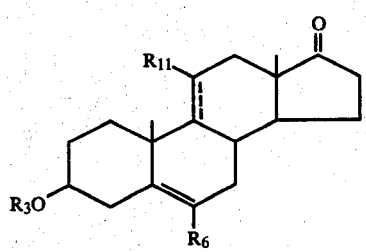
(ICa)

with a C₁₆ activating agent in the presence of an alkali metal alkoxide to produce an anion of a 16-substituted steroid of the formula

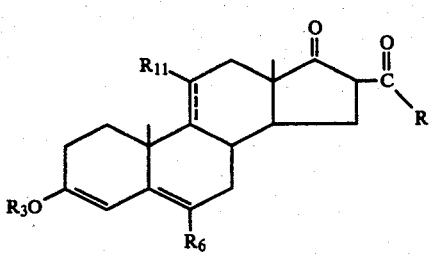
(IIAa)

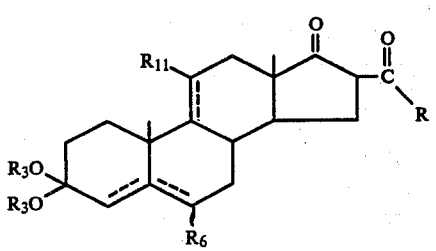
(IIAb)

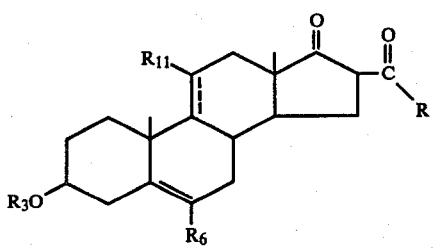
(IICa)

(2) contacting the anion of the 16-substituted steroid (II) from step (1) with a methylating agent to produce a 16-methyl-16-substituted steroid of the formula

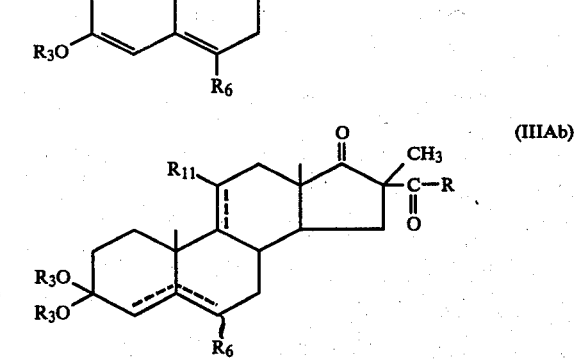
(IIIAa)

(IIIAb)

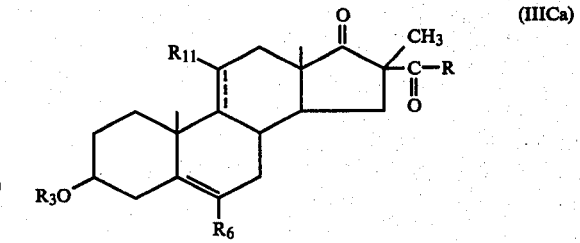
(IIICa)

and (3) contacting the 16-methyl-16-substituted steroid (III) from step (2) with a strong base in an alcohol containing solvent where R is a hydrogen atom or —CO—OR' or —OR';
R' is alkyl of 1 through 5 carbon atoms;
R₃ is alkyl of 1 through 5 carbon atoms;
R₆ is a hydrogen or fluorine atom,
R₁₁ is a hydrogen atom, nothing ($\Delta^{9(11)}$), or a hydroxyl group ($\alpha$ or $\beta$);
∼ indicates that the attached group can be in either the $\alpha$ or $\beta$ configuration; and
--- is a single or double bond.

2. A process according to claim 1 where the $\Delta^4$-3-keto steroid (A) is protected as the methyl enol ether, ethyl enol ether or ethylene ketal.

3. A process according to claim 1 where the $3\beta$-hydroxy-$\Delta^5$ steroid (C) is protected as the THP ether or methyl ether.

4. A process according to claim 1 where the C₁₆ activating agent is selected from the group consisting of dialkyloxalates, alkyl formates or dialkylcarbonates where the alkyl portion is 1 through 3 carbon atoms.

5. A process according to claim 4 where the C₁₆ activating agent is diethyloxalate or dimethyloxalate.

6. A process according to claim 1 where the alkali metal alkoxide is selected from the group consisting of lithium, sodium or potassium alkoxide where the alkyl portion is 1 through 4 carbon atoms.

7. A process according to claim 6 where the alkali metal alkoxide is sodium methoxide or sodium ethoxide.

8. A process according to claim 1 where the methylating agent is selected from the grop consisting of methyl iodide or methyl bromide.

9. A process according to claim 8 where the methylating agent is methyl iodide.

10. A process according to claim 1 where the strong base from the group consisting of alkali metal alkoxides, alkali metal hydroxides and alkali metal carbonates where the alkyl portion of the alkoxide is 1 through 4 carbon atoms.

11. A process according to claim 10 where the strong base is sodium methoxide.

12. A process according to claim 1 where the alcohol solvent is selected from the group consisting of alcohols of the formula ROH where R is alkyl of 1 through 5 carbon atoms.

13. A process according to claim 12 where the alcohol solvent is methanol.

14. A process for the preparation of a 16β-methyl-17-keto steroid of the formula

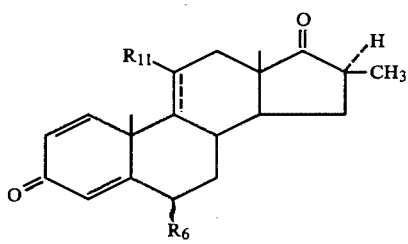

(IVB)

which comprises (1) contacting a 17-keto steroid of the formula

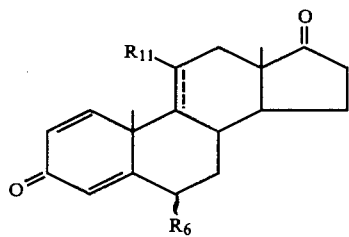

(IB)

with a $C_{16}$ activating agent in the presence of an alkali metal alkoxide to produce an anion of a 16-substituted steroid of the formula

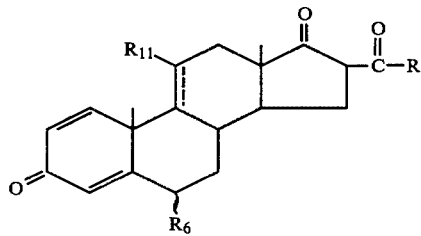

(IIB)

(2) contacting the anion of the 16-substituted steroid (IIB) with a methylating agent to produce a 16-methyl-16-substituted steroid of the formula

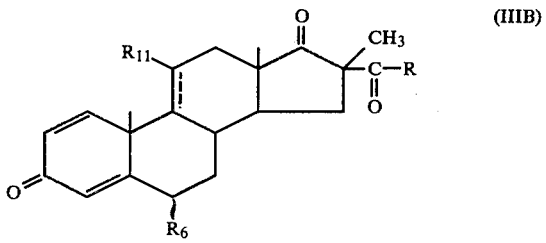

(IIIB)

and (3) contacting the 16-methyl-16-substituted steroid (IIIB) with a strong base in an alcohol containing solvent where R, $R_6$, $R_{11}$, ~ and --- are defined in claim 1.

15. A process according to claim 14 where the $C_{16}$ activating agent is selected from the group consisting of dialkyloxalates, alkyl formates or dialkylcarbonates where the alkyl portion is 1 through 3 carbon atoms.

16. A process according to claim 15 where the $C_{16}$ activating agent is diethyloxalate or dimethyloxalate.

17. A process according to claim 14 where the alkali metal alkoxide is selected from the group consisting of lithium, sodium or potassium alkoxide where the alkyl portion is 1 through 4 carbon atoms.

18. A process according to claim 17 where the alkali metal alkoxide is selected from the group consisting of sodium methoxide or sodium ethoxide.

19. A process according to claim 14 where the methylating agent is selected from the group consisting of methyl iodide or methyl bromide.

20. A process according to claim 19 where the methylating agent is methyl iodide.

21. A process according to claim 14 where the strong base from the group consisting of alkali metal alkoxides, alkali metal hydroxides and alkali metal carbonates where the alkyl portion of the alkoxide is 1 through 4 carbon atoms.

22. A process according to claim 21 where the strong base is sodium methoxide.

23. A process according to claim 14 where the alcohol solvent is selected from the group consisting of alcohols of the formula ROH where R is alkyl of 1 through 5 carbon atoms.

24. A process according to claim 23 where the alcohol solvent is methanol.

25. 3-Methoxy-16-methyl-16-(methyloxalyl)androst-3,5,9(11)-trien-17-one.

26. 3-Methoxy-16-methyl-16-(methyloxalyl)androst-3,5-dien-17-one.

* * * * *

UNITED STATES PATENT OFFICE
CERTIFICATE OF CORRECTION

Patent No. 4,451,404             Dated May 29, 1984

Inventor(s) Verlan H. VanRheenen and Joseph M. Timko

It is certified that error appears in the above-identified patent and that said Letters Patent are hereby corrected as shown below:

Column 4, line 29, "5 carbon atoms." should read --5 carbon atoms or THP.--
Column 5, line 1, "(IIIAa, Example 1)" should read --(IIAa, Example 1)--
Column 7, line 35, Chart A, " 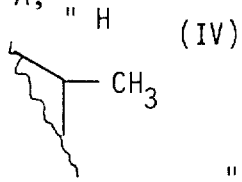   should be --  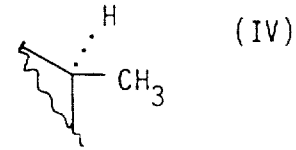  --

Column 7, line 60, Chart B "  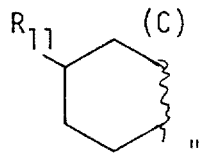   should be --  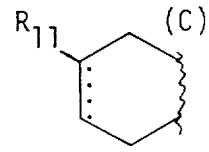  --

Column 11, line 2, "base from the group" should read --base is selected from the group--
Column 12, claim 21, line 39, "base from the group" should read --base is selected from the group--

Signed and Sealed this

Twenty-first Day of January 1986

[SEAL]

Attest:

DONALD J. QUIGG

Attesting Officer    Commissioner of Patents and Trademarks